United States Patent [19]
Maack et al.

[11] Patent Number: 5,643,867
[45] Date of Patent: Jul. 1, 1997

[54] METHOD FOR TREATING CATABOLIC CONDITIONS

[75] Inventors: Christopher A. Maack, El Cerrito; Andreas Sommer, Concord, both of Calif.

[73] Assignee: Celtrix Pharmaceuticals, Inc., Santa Clara, Calif.

[21] Appl. No.: 413,920

[22] Filed: Mar. 29, 1995

Related U.S. Application Data

[63] Continuation of Ser. No. 190,685, Feb. 1, 1994, abandoned, which is a continuation of Ser. No. 935,890, Aug. 26, 1992, abandoned.

[51] Int. Cl.$^6$ .................. C07K 14/62; A61K 38/28
[52] U.S. Cl. ............................ 514/3; 530/303
[58] Field of Search ....................... 530/350, 399, 530/303; 514/2, 3, 12

[56] References Cited

U.S. PATENT DOCUMENTS

| | | |
|---|---|---|
| 4,783,524 | 11/1988 | Larsen et al. . |
| 4,857,505 | 8/1989 | Arendt . |
| 4,857,506 | 8/1989 | Tyle . |
| 4,963,665 | 10/1990 | Rotwein et al. . |
| 5,077,276 | 12/1991 | Ballard et al. . |
| 5,126,324 | 6/1992 | Clark et al. . |
| 5,128,320 | 7/1992 | Hahn et al. . |
| 5,187,151 | 2/1993 | Clark et al. ............................ 514/3 |

FOREIGN PATENT DOCUMENTS

| | | |
|---|---|---|
| 0128733 | 12/1984 | European Pat. Off. . |
| 0379338 | 1/1990 | European Pat. Off. . |
| 0375438 | 6/1990 | European Pat. Off. . |
| WO9213556 | 8/1992 | WIPO . |
| WO92/18154 | 10/1992 | WIPO . |

OTHER PUBLICATIONS

Tesch et al., "Effects of free and bound insulin–like growth factors on proteoglycan metabolism in articular cartilage explants" *J. Orthopead. Res.* (1992) 10:14–22.

Hughes et al., "The induction of specific proteases for insulin–like growth factor–binding proteins following major heart surgery" *J. Endocrinol.* (1992) 135:135–145.

Blum et al., *Modern Concepts in Insulin–Like Growth Factors*, Spencer, E.M., Editor, (1991) Elsevier Publishers, New York, pp. 381–393.

Rinderknecht et al., *Proc. Natl. Acad. Sci.* (1976) 73:2365–2369.

Baxter et al., *Biochem. Biophys. Res. Comm.* (1986) 139:1256–1261.

Sommer et al., *Modern Concepts in Insulin–Like Growth Factors*, Spencer, E.M., Editor, (1991) Elsevier Publishers, New York, pp. 715–728.

The Veterans Affairs TPN Cooperative Study Group, *N. Engl. J. Med.* (1991) 325:525–532.

Jiang et al., *Ann. Surg.* (1989) 210:513–525.

Pape et al., *Chest* (1991) 99:1495–1500.

Hizuka et al., *European J. Pharmacol.* (1986) 125(1):143–146.

*Primary Examiner*—Dian C. Jacobson
*Assistant Examiner*—Karen Cochrane Carlson
*Attorney, Agent, or Firm*—Morrison & Foerster LLP

[57] ABSTRACT

This is a method for treating catabolic conditions in individuals by administering a composition containing a complex of insulin-like growth factor (IGF) and insulin-like growth factor binding protein-3 (IGFBP-3).

22 Claims, 1 Drawing Sheet

METHOD FOR TREATING CATABOLIC CONDITIONS

This application is a continuation of application Ser. No. 08/190,685, filed Feb. 1, 1994, which is a continuation of application Ser. No. 07/935,890, filed Aug. 26, 1992, both now abandoned.

DESCRIPTION

1. Technical Field

This invention relates to the treatment of metabolic disorders. This invention is a medical treatment for catabolic conditions in individuals with a loss of tissue protein. The method comprises administering a complex comprising an insulin-like growth factor (IGF) and insulin-like growth factor binding protein-3 (IGFBP-3).

2. Background Art

Growth factors are polypeptides which stimulate a wide variety of biological responses (e.g., DNA synthesis, cell division, expression of specific genes, etc.) in a defined population of target cells. A variety of growth factors have been identified including transforming growth factor-$\beta_1$ (TGF-$\beta_1$), TGF-$\beta_2$, TGF-$\beta_3$, epidermal growth factor (EGF), platelet-derived growth factor (PDGF), fibroblast growth factor (FGF), insulin-like growth factor-I (IGF-I), and IGF-II.

IGF-I and IGF-II are related in amino acid sequence and structure, with each polypeptide having a molecular weight of approximately 7500 daltons. IGF-I mediates the major effects of growth hormone and thus is the primary mediator of skeletal growth after birth. IGF-I has also been implicated in the actions of various other growth factors, since treatment of cells with such growth factors leads to increased production of IGF-I. In contrast, IGF-II is believed to have a major role in fetal growth. Both IGF-I and IGF-II have insulin-like activity (hence the name) and are mitogenic (stimulating cell division) for the cells in muscle, skeletal tissue and a wide variety of other tissues.

Unlike most growth factors, the IGFs are present in substantial quantity in the circulation, but only a very small fraction of this IGF is free in the circulation or in other body fluids. Most circulating IGF-I is bound to an IGF-binding protein called IGFBP-3. IGF-I may be measured in blood serum to diagnose abnormal growth-related conditions, e.g., pituitary gigantism, acromegaly, dwarfism, various growth hormone deficiencies, etc. Although IGF-I is produced in many tissues, most circulating IGF-I is believed to be synthesized in the liver.

Almost all IGF circulates in a non-covalently associated ternary complex composed of IGF-I or -II, an IGF specific binding protein termed IGFBP-3, and a larger protein termed the Acid Labile Subunit (ALS). This ternary complex is composed of equimolar amounts of each of the three components. The ALS has no direct IGF binding activity and appears to bind only a preformed IGF/IGFBP-3 complex. The ternary complex of IGF+IGFBP-3+ALS has a molecular weight of approximately 150,000 daltons. This ternary complex is alleged to function in the circulation "as a reservoir and a buffer for IGF-I and IGF-II preventing rapid changes of free IGF." See, Blum, W. F., et al., "Plasma IGFBP-3 Levels as Clinical Indicators", In *Modern Concepts in Insulin-Like Growth Factors*, E. M. Spencer, ed., Elsevier, N.Y., pages 381–393, 1991.

Nearly all of the IGF-I, IGF-II and IGFBP-3 in the circulation are in complexes, so very little free IGF or IGFBP-3 is detectable. Moreover, a high level of free IGF in plasma is undesirable. It would lead to serious hypoglycemia because IGF has insulin-like effects on circulating glucose levels. In contrast to the IGFs and IGFBP-3, there is a substantial pool of free ALS in plasma which assures that IGF/IGFBP-3 complex entering the circulation immediately forms a ternary complex.

IGFBP-3 is the most abundant IGF binding protein in the circulation, but at least five other distinct IGF binding proteins have been identified in various tissues and body fluids. Although these proteins bind IGFs, they each originate from separate genes and they have distinct amino acid sequences. Thus, the binding proteins are not merely analogs of a common precursor. Unlike IGFBP-3, the other IGFBPs in the circulation are not saturated with IGFs. None of the IGF binding proteins other than IGFBP-3 can form the 150 KD circulating ternary complex.

IGF-I and IGFBP-3 may be purified from natural sources or produced by recombinant means. For instance, IGF-I has been purified from human serum for a number of years. See, Rinderknecht, E. W., et al., *Proc Natl Acad Sci (USA)* 73, 2365–2369, 1976. Recombinant IGF-I processes are shown in EPA 0,128,733, published in December of 1984. IGFBP-3 may be purified from natural sources using a process such as that shown in Baxter et al., "Growth Hormone-Dependent Insulin-Like Growth Factors (IGF) Binding Protein from Human Plasma Differs from Other Human IGF Binding Proteins", *Biochem Biophys Res Comm* 139, 1256–1261, 1986. IGFBP-3 may be synthesized by recombinant organisms as discussed in Sommer, A. S., et al., In *Modern Concepts of Insulin-Like Growth Factors*, E. M. Spencer, ed., Elsevier, N.Y., pp. 715–728, 1991. This recombinant IGFBP-3 binds IGF-I in a 1:1 molar ratio. The topical administration of the IGF-I/IGFBP-3 complex to rat and pig wounds was significantly more effective than IGF-I alone. Sommer et al., ibid. Intravenous administration of the complex to hypophysectomized rats "substantially prevents the hypoglycemic effects of IGF-I" administered alone. Sommer et al., ibid.

U.S. Pat. No. 5,128,320 issued to Hahn et al. discloses a method for restoring weight gain and lean body mass in a mammal afflicted with glucocorticoid excess, which is endogenously or exogenously produced.

U.S. Pat. No. 5,126,324 issued to Clark et al. discloses a method for enhancing growth in a mammal by administration a combination of IGF-I and growth hormone (GH). Clark et al. mention that the technique is particularly useful in animals no longer responsive to GH alone.

Many patients have illnesses and other abnormalities that lead to debilitating catabolic states. Specifically, when people are chronically nutritionally deprived and/or expend an inordinate amount of calories (as in chronic obstructive pulmonary disease, or COPD), they burn body fat and protein. The protein comes from sacrificing needed enzymes and muscles. When protein is used for energy, the body excretes nitrogen. If patients who excrete nitrogen have a negligible intake of nitrogen-containing nutrients, such patients excrete more nitrogen than is ingested and therefore have a negative nitrogen balance. Catabolic conditions in which this occurs include, but are not limited to, chronic obstructive pulmonary disease, gastrointestinal tract resections or disorders, illnesses requiring corticosteroid therapy, diabetes, trauma, pneumonia, heart failure, stroke, cancer cachexia, and AIDS cachexia. Catabolism is associated with these illnesses and is characterized by negative nitrogen balance or protein wasting. Severe loss of body protein substantially increases chances for dying and/or prolonged hospitalization and major medical expenses.

An additional group of patients who are at risk of negative nitrogen balance are patients in hospitals or nursing homes who are convalescing from acute illnesses. Every year, several million elderly patients are hospitalized with problems running the gamut from pneumonia, to heart failure, broken bones, strokes, and cachexia due to tumors. Many of these patients cannot leave the hospital because they are too debilitated to ingest adequate nutrients to restore muscle mass and strength that would enable them to manage outside a hospital environment. Often, heroic measures such as total parenteral nutrition (TPN) are attempted to improve the prognosis for severely wasted patients. But in many instances, even TPN is not effective (The Veterans Affairs TPN Cooperative Study Group, *N Engl J Med* 325:525–32, 1991).

Increasing the circulatory level of growth hormone (Jiang, Z.-M., et al., *Ann Surg* 210, 513–525, 1989) or IGF-I (Pape, G. S., et. al., *Chest* 99, 1495–1500, 1991) has been shown to be effective in restoring or increasing positive nitrogen balance and in maintaining muscle mass in a variety of human and animal model studies. However, patients undergoing these treatments must be carefully monitored in order to avoid significant side effects.

DISCLOSURE OF INVENTION

In accordance with one embodiment of the present invention, there is provided a method for treating an individual for a catabolic condition, wherein the method comprises administering to an individual a complex comprising an insulin-like growth factor (IGF) and insulin-like growth factor binding protein-3 (IGFBP-3) in an amount sufficient to alleviate the catabolic condition.

In accordance with another embodiment of the present invention, the IGF used in the complex is provided as IGF-I. In a further embodiment, IGF and IGFBP are present in equimolar amounts. In still another embodiment, both IGF and IGFBP-3 are human proteins obtained from recombinant sources.

In accordance with another embodiment of the present invention, the complex of IGF and IGFBP-3 is administered by subcutaneous injection.

In yet another embodiment, the method of the present invention provides treatment of a protein wasting disease with a complex of IGF and IGFBP-3.

In another embodiment, the individual to whom the complex is administered is a mammalian or avian individual.

In yet another embodiment, the method provides for administration of the IGF/IGFBP-3 complex in an amount sufficient to result in a positive nitrogen balance. In a further embodiment, the amount of IGF/IGFBP-3 complex administered is at least about 0.05 to 10 mg of IGF/kg/day.

While not wishing to be bound by any particular theory, the Inventors propose that the administered complex of IGF and IGFBP-3 results in the gradual release of free IGF in somewhat elevated levels. The added IGF is believed to promote cell anabolism and thereby alleviate the continuing loss of muscle mass and strength in catabolic conditions and promote restoration of muscle mass and strength.

MODES FOR CARRYING OUT THE INVENTION

Definitions

Figure 1:
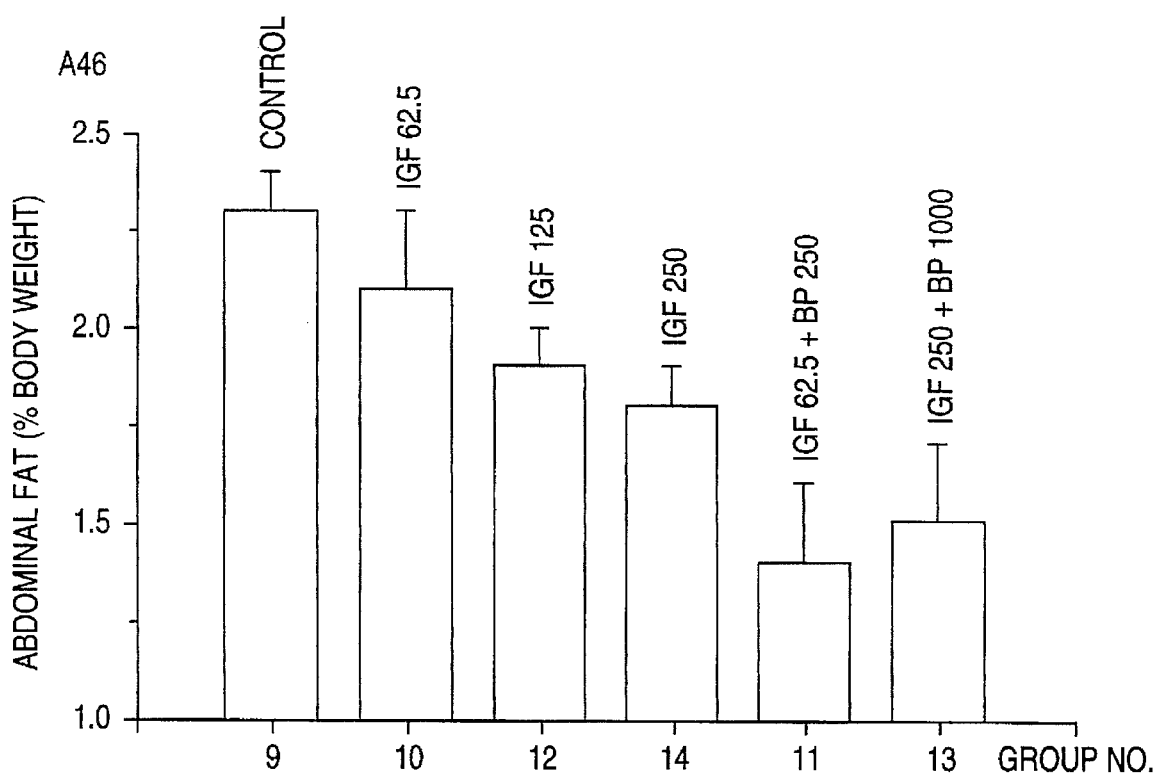
FIG. 1 is a bar graph depicting the results of various treatments (including the inventive treatment) on broiler chickens.

As used herein, "nitrogen balance" is defined as the comparison of nitrogen intake with nitrogen excretion. A positive nitrogen balance is achieved when a patient takes in more nitrogen than is excreted. A negative nitrogen balance occurs when there is tissue breakdown and the individual excretes more nitrogen than is taken in.

A "catabolic condition" is one in which an individual has a net breakdown of tissue. This contrasts with an anabolic state in which an individual has a net increase in body tissue, such as increasing muscle mass.

"Individuals" are defined as humans and mammal and avian farm animals, sport animals and pets. Farm animals include, but are not limited to, cows, hogs, sheep, chicken, turkeys, ducks and geese. Sport animals include, but are not limited to, dogs and horses. The category pets includes, but is not limited to, cats, dogs, and birds.

"Insulin-like growth factor (IGF)" comprises a family of factors, including but not limited to IGF-I and IGF-II. IGF is a polypeptide having a molecular weight of about 7500 daltons. IGF may be obtained from natural sources or prepared by recombinant means.

"Insulin-like growth factor binding protein (IGFBP)" comprises a family of binding proteins, including but not limited to IGFBP-1, IGFBP-2, IGFBP-3, IGFBP-4, IGFBP-5 and IGFBP-6. IGFBP may be obtained from natural sources or prepared by recombinant means. At least one form of IGFBP (for example, IGFBP-3) complexes with IGF and with a third molecule known as ALS.

A "therapeutic composition" as used herein is defined as comprising IGF complexed with its binding protein IGFBP-3. The therapeutic composition may also contain excipients such as water, minerals and carriers such as protein.

The method of the present invention contemplates treating and alleviating the catabolic state associated with a variety of diseases by administering a complex of IGF and IGFBP-3. Nearly all IGF-I or IGF-II complex with IGFBP-3 and IGF/IGFBP-3 normally circulate in the form of a complex in humans and other mammals and avians. This complex associates with a third protein (ALS), which is present in excess over the concentration of IGF and IGFBP-3. Therefore, ALS is found both associated with the IGF/IGFBP-3 complex and in the free form. The resultant ternary complex has a size of about 150 kD. Administration of the complex of IGF and IGFBP-3, either from natural or recombinant sources, as a preformed complex results in the formation of the ternary complex with the normally excess ALS. This type of treatment appears to produce a long term increase in the level of circulating IGF, which is gradually released from the ternary complex. This mode of administration avoids the detrimental side effects associated with administration of free IGF-I, e.g., hypoglycemia, suppression of growth hormone and ALS production, and release of endogenous IGF-II since administered exogenous free IGF-I replaces endogenous IGF-II in normally circulating IGF-II/IGFBP-3 complexes.

The formulation, method of administration and dosage will depend upon the disorder to be treated, and the medical history of the patient. These factors are readily determinable in the course of therapy. Suitable patients with a catabolic disorder or wasting disease can be identified by medical history, physical findings and laboratory tests. The medical history may reveal such facts as recent weight loss, decreasility to perform normal functions of life, and illness or
 . Patients may have physical findings such as low
 for their age and height, low abdominal or triceps
 old thickness, low hand-grip strength, low arm-muscle
circumference and poor pulmonary function due to weakened respiratory muscles. Indicative laboratory results include low levels of serum prealbumin and albumin and abnormally high levels of nitrogenous wastes in the urine. When the amount of excreted nitrogen exceeds the nitrogen intake, the patient is in negative nitrogen balance.

In accordance with the method of the present invention, the formulation comprises a complex of IGF and IGFBP-3. Preferably, the IGF is IGF-I, although IGF-II may be useful. Because IGF and IGFBP-3 naturally complex in a 1:1 molar ratio, a composition of equimolar amounts of IGF and IGFBP-3 is preferred. The product can be formulated with IGF:IGFBP-3 molar ratios ranging from 0.5 to 1.5. More preferably, the molar ratio is 0.9 to 1.3; and most preferably, the product is formulated with approximately a 1:1 molar ratio.

In accordance with the method of the present invention, IGF and IGFBP-3 are human proteins obtained from natural or recombinant sources. Most preferably, IGF and IGFBP-3 are human IGF-I and IGFBP-3 made by recombinant means and designated rhIGF-I and rhIGFBP-3, respectively. rhIGFBP-3 may be in glycosylated or non-glycosolated form. *E. coli* is a source of the non-glycosolated IGFBP-3. Glycosylated IGFBP-3 may be obtained from CHO-cells.

The method of the present invention provides for formulating the complex in modes which are readily apparent to those skilled in the art. Preferably, the IGF and IGFBP-3 are complexed prior to administration to the treated individual. Preferably, the complex is formed by mixing approximately equimolar amounts of IGF-I and IGFBP-3 dissolved in physiologically compatible carriers such as normal saline solution or phosphate buffered saline solution. Most preferably, a concentrated solution of rhIGF-I and a concentrated solution of IGFBP-3 are mixed together for a sufficient time to form an equimolar complex.

Depending on the mode of administration, compositions of the complex may be in the form of solid, semi-solid or liquid dosage preparations, such as for example, tablets, pills, powders, capsules, liquids, suspensions or the like. Physiologically compatible carriers include intravenous solutions, such as normal saline, serum albumin, 5% dextrose, plasma preparations, other protein-containing solutions and TPN solutions. The preferred carrier for parenteral administration of the complex is a sterile, isotonic aqueous solution, such as normal saline or 5% dextrose. Alternatively, a solution of the complex may be placed into an implant, such as an osmotic pump, for the slow release of the complex over an extended period of time. Alternatively, the complex may be provided in sustained release carrier formulations such as semi-permeable polymer carriers in the form of suppositories or microcapsules. See, for instance, U.S. Pat. No. 3,773,919 for Microcapsular Sustained Release Matrices Including Polylactides; Sidmon et al., *Biopolymers* 22 (1), 547–556 (1983) for copolymers of L-glutamic acid and γ-ethyl-L-glutamate; Langer et al., *J Biomed Res* 15, 167–277 (1981) for poly(2-hydroxyethylmethacrylate) or the like.

The mode of administration delivers the complex to the individual in a safe, physiologically effective manner. The complex may be given by intranasal, subcutaneous, intravenous, intraperitoneal, or other conventional routes of administration. Preferably, the complex is injected subcutaneously, intravenously or intramuscularly. Most preferably, the complex is administered by subcutaneous injection. By subcutaneous injection, the complex appears not to be toxic or mitogenic at the injection site. In another preferred mode of administration, the complex is administered by continuous intravenous infusion in combination with TPN solutions.

The dose of complex to be administered can be readily determined by those skilled in the art, based on the usual patient symptoms discussed above. Preferably, when the complex is administered to humans daily, the dosage of complex is at least about 0.05 mg IGF/kg of body weight/day, complexed to an equimolar amount of IGFBP-3. More preferably, the daily dosage of the complex for humans is at least 0.1 mg IGF/kg/day, complexed to an equimolar amount of IGFBP-3. If daily dosages in excess of about 0.5 mg IGF/kg must be given, the dosage may be divided and injected subcutaneously at two or more sites.

If the IGF/IGFBP-3 complex were administered to humans twice a week, each dose of complex is preferably at least about 0.1 mg IGF/kg of body weight, complexed to an equimolar amount of IGFBP-3. More preferably, for twice weekly administration, the dose of the complex is at least 0.5 mg IGF/kg, complexed to an equimolar amount of IGFBP-3. There is no known upper limit of dosage; however, it is preferable that a single dose not exceed 10 mg IGF/kg of body weight, when the IGF is complexed to an equimolar amount of IGFBP-3. These doses of IGF/IGFBP-3 complex are not expected to cause significant hypoglycemia since IGFBP-3 slows the IGF binding to cellular insulin receptors.

Preferably, the malnourished patient is started with a relatively low dose of the complex, such as 0.05 mg of IGF-I complexed with an equimolar amount of IGFBP-3/kg of body weight/day. The various factors given above should be monitored to determine if there is improvement. Preferably, the patient's nitrogen balance becomes positive. If the patient improves with the low dose, the low dose preferably should be continued until the patient's wasting is ameliorated or nutritional status is adequately improved, as indicated by the physical findings and laboratory results described above. For example, hand-grip strength and/or pulmonary function should improve. Such improvement may be evident in two to three weeks.

If the patient's nitrogen balance does not become positive after the low dose of the complex, the dose preferably should be increased gradually until the nitrogen balance becomes positive.

Somewhat higher per kilogram doses are needed for small animals receiving the IGF/IGFBP-3 complex. For example, a bird may be dosed twice a week with about 0.05 to 1.0 mg of IGF/kg of body weight.

The invention has been disclosed by direct description. The following are examples showing the efficacy of the method in increasing muscle mass and lean body mass. The examples are only examples and should not be taken in any way as limiting to the scope of the method.

EXAMPLES

Example 1

This experiment shows the effect of the complex of IGF-I and IGFBP-3 upon lean body mass production as opposed to fat production. In this experiment, human recombinant IGF-I and IGFBP-3 were used. The rhIGF-I (Ciba-Geigy) was synthesized in yeast and provided in sterile water and stored at −70° C. The rhIGFBP-3 (Celtrix Laboratories, Inc., Santa Clara, Calif.) was synthesized by *E. coli* and was not glycosylated; IGFBP-3 was dissolved in phosphate-buffered saline and stored at −70° C. until use. Prior to administration, the proteins were thawed, and sufficient amounts of IGF-I and IGFBP-3 were mixed to provide equimolar amounts of the two proteins. Groups of growing broiler chickens were treated with various doses of free IGF-I or IGF-I/IGFBP-3 complex. A control group of chickens was treated only with placebo or the vehicle. All treatments were administered by subcutaneous injection three times a day. The doses were administered for two weeks between days 25 and 39 of life, when the chickens were still growing.

The overall growth rate of the animals was not affected by treatment with free IGF-I or IGF-I/IGFBP-3 complex at any dose level. However, the effect on the accumulation of fat in the abdominal fat pad, as illustrated in FIG. 1, was quite striking. Treatment with free IGF-I at daily doses of 62.5, 125 or 250 µg/kg (Groups 10, 12 and 14, respectively) resulted in a progressive decrease in abdominal fat pad weight as a percentage of total body weight compared to control animals treated with vehicle (Group 9). Surprisingly, when IGF-I was administered with IGFBP-3 in the IGF-I/IGFBP-3 complex, a much larger effect was obtained. The lowest daily dose of IGF-I/IGFBP-3 complex (62.5 µg IGF-I/kg+250 µg IGFBP-3/kg, Group 11) resulted in the largest decrease in abdominal fat pad weight. This fat reduction amounted to a decrease of 40% in the weight of fat pads of treated animals compared to those of control animals. This decrease in fat pad weight could not be equalled by even a four-fold higher dose of free IGF-I. This may be the maximum fat pad reduction obtainable, as the higher dose of IGF-I/IGFBP-3 complex did not lead to further reduction.

Because IGF is not known to have a preferential effect on abdominal fat pads over other body fat, we expected that the decreased deposition of fat in the abdominal fat pad reflects fat reduction in the rest of the body. Since overall body weight gain was not affected by these treatments, and no obvious edema was observed, we expect that body fat reductions were balanced by increases in lean body mass in treated animals. And this was confirmed by the experiment in Example 2.

Example 2

This example shows the use of free IGF-I and the IGF-I/IGFBP-3 complex on female rats with ovariectomy-induced osteoporosis. Both rhIGF-I and rhIGFBP-3 were obtained as mentioned above. This experiment demonstrates the ability of the IGF-I/IGFBP-3 complex to increase muscle mass and lower fat mass.

In this example, young female rats of 90–100 g body weight were ovariectomized by the dorsal route and were divided into six groups of eight animals each. An additional group consisted of eight intact, age-matched sham operated control rats. Six weeks after ovariectomy, treatment of the animals was started as follows:

Group 1: Sham Operated Controls; Vehicle

Group 2: Ovariectomized Controls; Vehicle

Group 3: Ovariectomized; 2.5 mg/kg IGF-I complexed to 9.5 mg/kg IGFBP-3

Group 4: Ovariectomized; 0.25 mg/kg IGF-I complexed to 0.95 mg/kg IGFBP-3

Group 5: Ovariectomized; 0.025 mg/kg IGF-I complexed to 0.095 mg/kg IGFBP-3

Group 6: Ovariectomized; 2.5 mg/kg IGF-I

Group 7: Ovariectomized; 0.25 mg/kg IGF-I

The complex was formed by mixing equimolar amounts of IGFBP-3 (dissolved in phosphate buffered saline (PBS), pH 6.0) and IGF-I (dissolved in 10 Mm sodium acetate, pH 5.5) in the minimum volume feasible, and incubating the mixture overnight at 4° C. The complex was then diluted with PBS, pH 6.0, containing 0.1% rat serum albumin. The solutions were divided into aliquots containing the amount of material needed for one day, and stored at −70° C. until needed. The controls received the dilution buffer.

The animals were treated for 22 days. The test substances were administered six times per week by one daily subcutaneous injection. One day before treatment was started and on the 17th day of treatment, 20 mg/kg of calcein was given by intraperitoneal injection. Calcein is a tetracycline which deposits in growing bone and is used to estimate the amount of bone growth between its administrations. Similarly, on the tenth day 20 mg/kg of demeclocycline was administered. On day 23, 24 hours after the last injection, the animals were killed by anesthesia with carbon dioxide.

The body weight was recorded throughout the experiment. At autopsy, 0.1 ml of blood was taken for the determination of blood glucose. Serum was prepared from the rest of the blood, and total serum IGF-I levels were determined by RIA. Gastrocnemius muscle, periuterine fat and uterus were removed, dissected free of connective tissue, and weighed.

The results of this experiment are detailed in Tables 1 and 2 and summarized below.

When ovariectomized ("Ovx" in the tables) control animals were compared to sham operated control animals, no significant differences were observed in serum IGF-I levels or in daily body weight gain (Tables 1 and 2). Gastrocnemius muscle mass was increased by 22% and periuterine fat mass by 48% in ovariectomized controls (Table 2), while trabecular bone weight, calcium and hydroxyproline were substantially reduced (data not shown).

In ovariectomized animals treated with IGF-I/IGFBP-3 complex, the concentration of plasma IGF-I was increased in a dose dependent manner by the three doses of the complex, namely by 14, 32 and 47%, respectively (Table 1).

TABLE 1

| | Treatment Groups | | | | | | |
|---|---|---|---|---|---|---|---|
| | Group 1 (Sham Operated) | Group 2 (Ovx Control) | Group 3 | Group 4 | Group 5 | Group 6 | Group 7 |
| IGF-I (mg/kg) | — | — | 2.5 | 0.25 | 0.025 | 2.5 | 0.25 |
| IGFBP-3 | — | — | 9.5 | 0.95 | 0.95 | — | — |

TABLE 1-continued

| | Treatment Groups | | | | | | |
|---|---|---|---|---|---|---|---|
| | Group 1 (Sham Operated) | Group 2 (Ovx Control) | Group 3 | Group 4 | Group 5 | Group 6 | Group 7 |
| (mg/kg) Serum Parameters[1] | | | | | | | |
| IGF-I (ng/ml) | 292 ± 35 | 275 ± 26 | 403 ± 130 | 363 ± 49 | 314 ± 20 | 350 ± 49 | 341 ± 89 |
| (%) | (+6) | — | (+47) | (+32) | (+14) | (+27) | (+24) |
| Blood glucose (mmol/l) | 5.54 ± 0.07 | 6.21 ± 0.07 | 6.37 ± 0.27 | 6.23 ± 0.12 | 6.30 ± 0.12 | 5.88 ± 0.19 | 6.37 ± 0.12 |
| (%) | (−11) | — | (+3) | (±0) | (+1) | (−5) | (+3) |

[1]% are compared to ovariectomized, vehicle treated control values (Group 2)

TABLE 2

| | Treatment Groups | | | | | | |
|---|---|---|---|---|---|---|---|
| | Group 1 (Sham Operated) | Group 2 (Ovx Control) | Group 3 | Group 4 | Group 5 | Group 6 | Group 7 |
| IGF-I (mg/kg) | — | — | 2.5 | 0.25 | 0.025 | 2.5 | 0.25 |
| IGFBP-3 (mg/kg) | — | — | 9.5 | 0.95 | 0.95 | — | — |
| Body Composition[1] | | | | | | | |
| Body wght gain (g/day) | 1.24 ± 0.33 | 1.24 ± 0.07 | 1.46 ± 0.30 | 1.03 ± 0.11 | 0.67 ± 0.13 | 1.75 ± 0.33 | 0.84 ± 0.11 |
| (%) | (±0) | — | (+18) | (−17) | (−46) | (+41) | (−32) |
| Peri-uterine fat (g) | 4.45 ± 0.98 | 6.57 ± 0.72 | 5.07 ± 0.76 | 5.73 ± 0.90 | 6.64 ± 0.94 | 6.77 ± 0.89 | 6.78 ± 0.67 |
| (%) | (−32) | — | (−23) | (−13) | (+1) | (+3) | (+3) |
| Muscle | 3.67 ± 0.17 | 4.48 ± 0.14 | 5.03 ± 0.21 | 4.70 ± 0.16 | 4.56 ± 0.15 | 4.95 ± 0.25 | 4.48 ± 0.15 |
| (%) | (−18) | — | (+12) | (+5) | (+2) | (+10) | (±0) |

[1]% are compared to ovariectomized, vehicle treated control values (Group 2)

However, due to large variations in the measured values, none of these increases reached statistical significance. This was most likely due to the fact that the samples were taken 24 hours after the last treatment, at which time expected early increases in circulating IGF-I apparently dissipated.

In the rats treated with IGF-I/IGFBP-3 complex, body weight gain was affected biphasically (Table 2). In the group receiving the lowest dose of IGF-I/IGFBP-3 complex, weight gain was reduced by 46%; but in the groups receiving the medium and highest doses, there was no statistically significant change in weight gain.

The trends toward a dose-dependent increase in the weight of the gastrocnemius muscle and a dose-dependent decrease in the weight of periuterine fat with increasing IGF-I/IGFBP-3 complex were apparent (Table 2). At the highest complex dose, muscle mass was increased by 12% above the muscle mass increase observed as a result of ovariectomy alone. Conversely, at the highest complex dose, periuterine fat mass was decreased by 23%, substantially reversing the increase in fat mass resulting from ovariectomy.

Free IGF-I at a dose of 2.5 mg/kg also increased muscle mass, but the increase was not statistically significant; and essentially no effect was seen at a dose of 0.25 mg/kg. Furthermore, neither dose of free IGF-I had an effect on periuterine fat mass.

The combination of the increase in muscle, decrease in fat, and overall maintenance of total body weight indicates the potent effects of the IGF-I/IGFBP-3 complex in promoting muscle accretion and lean body mass development, and demonstrates the effectiveness of the complex.

This invention has been detailed both by example and by direct description. It should be apparent that one having ordinary skill in this art would be able to surmise equivalents to the invention as described in the claims which follow but which would be within the spirit of the description above. Those equivalents are to be included within the scope of this invention.

We claim:

1. A method for treating a protein wasting disease, said method comprising administering parenterally to an individual in need of such treatment a complex comprising insulin-like growth factor (IGF) and insulin-like growth factor binding protein (IGFBP-3), said complex administered in an amount sufficient to alleviate said disease as indicated by an increase in lean body mass of said individual, and wherein said parenteral administration is selected from the group consisting of intramuscular, intranasal, intraperitoneal, and intravenous administration.

2. The method of claim 1, wherein the complex comprises an equimolar amount of IGF and IGFBP-3.

3. The method of claim 1, wherein the IGF is IGF-1.

4. The method of claim 1, wherein the IGF is IGF-II.

5. The method of claim 1, wherein the IGF is human IGF.

6. The method of claim 1, wherein the amount of complex administered is at least about 0.05 mg of IGF/kg of body weight/day.

7. The method of claim 1, wherein said individual is a mammalian or avian individual.

8. A method for treating a catabolic disease, said method comprising administering parenterally to an individual in need of such treatment a complex comprising insulin-like growth factor (IGF) and insulin-like growth factor binding protein (IGFBP-3), said complex administered in an amount sufficient to alleviate said disease as indicated by an increase in lean body mass of said individual, and wherein said parenteral administration is selected from the group consisting of intramuscular, intranasal, intraperitoneal, and intravenous administration.

9. The method of claim 8, wherein the complex comprises an equimolar amount of IGF and IGFBP-3.

10. The method of claim 8, wherein the IGF is IGF-1.

11. The method of claim 8, wherein the IGF is IGF-II.

12. The method of claim 8, wherein the IGF is human IGF.

13. The method of claim 8, wherein the amount of complex administered is at least about 0.05 mg of IGF/kg of body weight/day.

14. The method of claim 8, wherein said individual is a mammalian or avian individual.

15. The method of claim 1, wherein the parental administration is intramuscular administration.

16. The method of claim 1, wherein the parental administration is intranasal administration.

17. The method of claim 1, wherein the parental administration is intraperitoneal administration.

18. The method of claim 1, wherein the parental administration is intravenous administration.

19. The method of claim 8, wherein the parental administration is intramuscular administration.

20. The method of claim 8, wherein the parental administration is intranasal administration.

21. The method of claim 8, wherein the parental administration is intraperitoneal administration.

22. The method of claim 8, wherein the parental administration is intravenous administration.

* * * * *